United States Patent
Goruganthu et al.

(10) Patent No.: US 6,421,811 B1
(45) Date of Patent: *Jul. 16, 2002

(54) DEFECT DETECTION VIA ACOUSTIC ANALYSIS

(75) Inventors: Rama R. Goruganthu; Jeffrey D. Birdsley; Michael R. Bruce; Brennan V. Davis; Rosalinda M. Ring, all of Austin, TX (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/409,498

(22) Filed: Sep. 30, 1999

(51) Int. Cl.$^7$ .................. G06F 17/50; G06F 19/00; G10K 11/04; G10K 15/10; G01R 31/26

(52) U.S. Cl. ............... 716/4; 700/110; 702/59; 702/103; 702/118; 324/520; 324/765

(58) Field of Search ............... 716/1–21; 700/100–110; 702/54, 58–59, 103, 117–118; 324/512, 520, 537, 765

(56) References Cited

U.S. PATENT DOCUMENTS

| | | | | |
|---|---|---|---|---|
| 4,618,934 A | * | 10/1986 | Nagase .................. | 382/149 |
| 4,831,565 A | * | 5/1989 | Woodward ............... | 702/103 |
| 5,101,162 A | * | 3/1992 | Webster et al. .......... | 324/618 |
| 5,608,526 A | | 3/1997 | Piwonka-Corle et al. ... | 356/369 |
| 5,633,747 A | | 5/1997 | Nikoonahad ............. | 359/312 |
| 5,719,495 A | * | 2/1998 | Moslehi ................. | 324/158.1 |
| 5,760,904 A | * | 6/1998 | Lorraine et al. .......... | 356/360 |
| 5,771,094 A | | 6/1998 | Carter et al. ............. | 356/326 |
| 5,796,004 A | * | 8/1998 | Nakaso et al. ........... | 73/643 |
| 5,840,023 A | | 11/1998 | Oraevsky et al. ......... | 600/407 |
| 6,069,366 A | | 5/2000 | Goruganthu et al. ...... | 250/559.27 |
| 6,182,510 B1 | * | 2/2001 | Stanke et al. ............ | 73/597 |
| 6,253,621 B1 | * | 7/2001 | Jarvis ................... | 73/655 |
| 6,301,967 B1 | * | 10/2001 | Donskoy et al. .......... | 73/579 |

OTHER PUBLICATIONS

NB84124370 ("Detection of Circuit Board Via Defects by Acousto–Electric (Micro–Phonic) Means", IBM Technical Disclosure Bulletin, vol. 27, No. 7B, Dec. 1984, pp. 4370–4372 (4 pages)).*

Deletage et al. ("Thermomechanical behavior of ceramic ball grid array based on experiments and FEM simulations", Nineteenth IEEE/CPMT Electronics Manufacturing Technology Symposium, Oct. 14, 1996, pp. 91–98).*

Semmens et al. ("Nondestructive evaluation of debonding within plastic integrated circuit packages using different methods of acoustic microscopy", 7th IEEE/CHMT International Electronic Manufacturing Technology Symposium, Sep. 25, 1989, p. 322).*

NN87024105 ("Non–Destructive, Non–Contacting Test of Si Wafers by Thermore–Flectance", IBM Technical Disclosure Bulletin, vol. 29, No. 9, Feb. 1987, pp. 4105–4113 (14 pages)).*

A. Grossman et al., "A new millimeter free electron laser using a relativistic beam with spiraling electrons," Phys. Fluids 26(1), Jan. 1983, 1983 American Institute of Physics, pp. 337–343.

S. T. Zavtrak, "Free gas bubbles acoustic laser," The Institute of Nuclear Problems, Bobruiskaya Str., 11, Minsk 220050, Belarus, 1995 Elsevier Science B. V., A358(1995) pp. 473–474.

* cited by examiner

*Primary Examiner*—Matthew Smith
*Assistant Examiner*—Phallaka Kik

(57) ABSTRACT

According to an example embodiment of the present invention, a defect detection approach involves detecting the existence of defects in an integrated circuit as a function of acoustic energy. Acoustic energy propagating through the device is detected. A parameter including information such as amplitude, frequency, phase, or a spectrum is developed from the detected energy and correlated to a particular defect in the device.

19 Claims, 2 Drawing Sheets

DEFECT DETECTION VIA ACOUSTIC ANALYSIS

RELATED APPLICATIONS

The present invention is related to U.S. patent application Ser. No. 09/410,147 entitled "ACOUSTIC THREE DIMENSIONAL ANALYSIS OF CIRCUIT STRUCTURES" and filed concurrently herewith, and to U.S. patent application Ser. No. 09/387,182 entitled "MICRO-VOID DETECTION" and filed on Aug. 31, 1999, now U.S. Pat. No. 6,253,621, which are incorporated herein by reference.

FIELD OF THE INVENTION

The present invention relates generally to semiconductor devices and their fabrication and, more particularly, to semiconductor devices and their manufacture involving testing the devices for defects.

BACKGROUND OF THE INVENTION

The semiconductor industry has recently experienced technological advances that have permitted dramatic increases in circuit density and complexity, and equally dramatic decreases in power consumption and package sizes. Present semiconductor technology now permits single-chip microprocessors with many millions of transistors operating at speeds of hundreds of millions of instructions per second to be packaged in relatively small, air-cooled semiconductor device packages. A by-product of such high-density and high functionality has been an increase in the number and complexity of the manufacturing processes, as well as an increase in the difficulties of maintaining satisfactory levels of quality control, testing the devices for defects, and providing a cost-effective product using such processes.

As the manufacturing processes for semiconductor devices and integrated circuits increase in difficulty, methods for testing and debugging these devices become increasingly important. Not only is it important to ensure that individual chips are functional, it is also important to ensure that batches of chips perform consistently. In addition, the ability to detect a defective manufacturing process early is helpful for reducing the number of defective devices manufactured.

Traditionally, integrated circuits have been tested using methods including directly accessing circuitry or devices within the integrated circuit. In addition, many methods require the circuit to be powered. Directly accessing the circuitry is difficult for several reasons. For instance, in flip-chip type dies, transistors and other circuitry are located in a very thin epitaxially-grown silicon layer in a circuit side of the die. The circuit side of the die is arranged face-down on a package substrate. This orientation provides many operational advantages. However, due to the face-down orientation of the circuit side of the die, the transistors and other circuitry near the circuit side are not readily accessible for testing, modification, or other purposes. Therefore, access to the transistors and circuitry near the circuit side is from the back side of the chip.

Since access to the transistors and circuitry in flip-chips is generally from the back side of the device, it is often necessary to mill through the back side and probe certain circuit elements in order to test the device. Milling through the back side is often difficult and time consuming. Moreover, circuitry and devices in the integrated circuit may potentially be damaged by milling processes. The difficulty, cost, and destructive aspects of existing methods for testing integrated circuits are impediments to the growth and improvement of semiconductor technologies.

SUMMARY OF THE INVENTION

The present invention is exemplified in a number of implementations and applications, some of which are summarized below. According to an example embodiment, the present invention is directed to a method for testing an integrated circuit. Acoustic energy propagation in the integrated circuit is detected and circuit defects are detected as a function of the acoustic energy.

According to another example embodiment of the present invention, a system is arranged for testing an integrated circuit having circuitry in a circuit side opposite a back side The system includes a substrate removal device and a laser configured and arranged to excite circuitry in the integrated circuit. One or more acoustic energy detectors are used to detect acoustic energy. A computer is configured and arranged to use the detected acoustic energy and generate a parameter that can be used to detect one or more defects in the integrated circuit. For example, the defect can be detected at the computer, or it can be detected via an outside source, such as a human operator viewing a computer-generated parameter. In another example embodiment, the computer, the laser, and the acoustic energy detectors are communicatively coupled.

The above summary of the present invention is not intended to describe each illustrated embodiment or every implementation of the present invention. The figures and detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
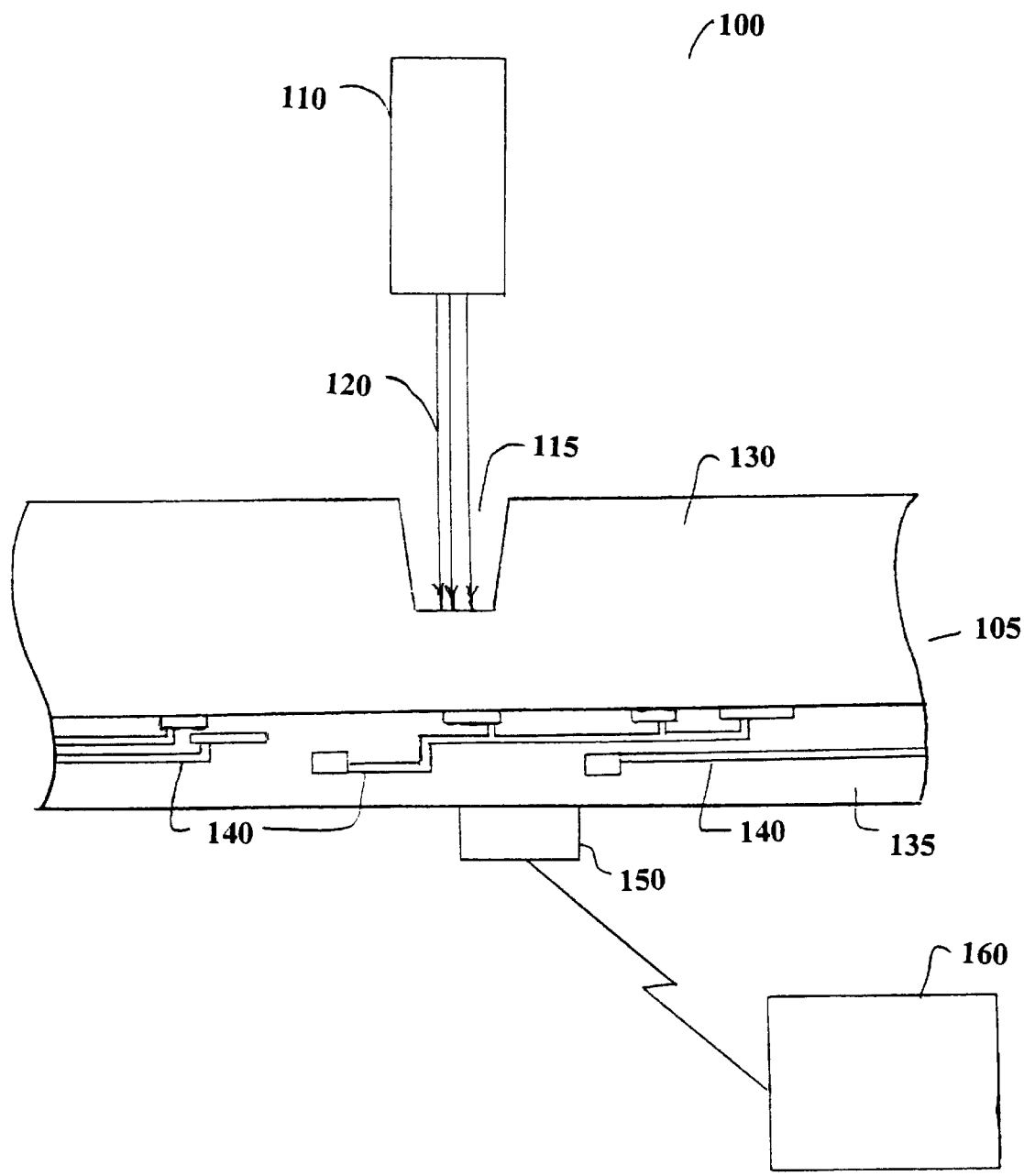
FIG. 1 shows an integrated circuit device undergoing testing, according to an example embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

The present invention is believed to be applicable to a variety of different types of semiconductor devices requiring or benefiting from defect analysis. The invention has been found to be particularly suited for post-manufacturing failure analysis of semiconductor devices having target circuitry containing defects such as shorts and opens in the circuit structure. While the present invention is not necessarily limited to such devices, various aspects of the invention may be appreciated through a discussion of various examples using this context.

According to an example embodiment of the present invention, acoustic energy propagation in an integrated circuit is detected. It has been discovered that acoustic energy propagation in integrated circuits varies relative to defects in the circuit. In this manner, the detected acoustic energy propagation is used to detect the existence of defects in the integrated circuit.

According to a more particular example embodiment, and referring to FIG. 1, a system 100 is used and a target region 115 of the back side 130 of an integrated circuit die 105 having a back side opposite circuitry 140 in a circuit side 135 is thinned. The device may be thinned, for example, using a laser etching device, a FIB, chemical-mechanical polishing, or other suitable removal device. A laser device 110 is used and a laser beam 120 of a wavelength of about 1064 nanometers is directed at the thinned portion of the back side 130 and optical beam induced current (OBIC) is created, resulting in pn junction activity. OBIC occurs when electron-hole pairs are generated in the die substrate and the photo-generated carriers diffuse to a depletion region. Electron-hole pairs may also be created directly in the depletion region by the laser, contributing to the OBIC. The OBIC generates acoustic energy that varies in relation to the mass of circuitry coupled to the region in which the OBIC is created. The acoustic energy is detected via detector 150 and used for defect analysis at a computer arrangement 160. The detector 150 may include, for example, an acoustic transducer such as an UltraSonic Transducer available from Sonix, Inc.

For instance, when there is a short circuit in the portion of circuitry in the die coupled to the region in which OBIC is generated, more circuitry is affected by the OBIC via the short. This additional circuitry effectively increases the amount of circuit mass affected by the OBIC as compared to the amount of affected circuitry without the short. As the mass increases, both the frequency and amplitude of the acoustic energy propagation decrease, and the wave propagates slower, delaying the phase. The phase may be detected by synchronizing the acoustic detector with the laser. Using this same approach, open circuits in circuitry within the device reduce the amount of metal mass affected by the OBIC as compared to circuitry not having an open. As the circuit mass decreases, both the frequency and amplitude of the acoustic energy propagation increase, and the phase is advanced. Therefore, a die can be tested using OBIC and, based on a variation in at least one frequency, amplitude, or phase parameter, shorts and opens can be detected. The parameter variations may, for example, be determined by comparing the parameter to a standard parameter developed from a non-defective die. This method includes additional advantages in that it does not require the device to be powered, nor does it require direct access to circuitry within the device.

Figure 2:
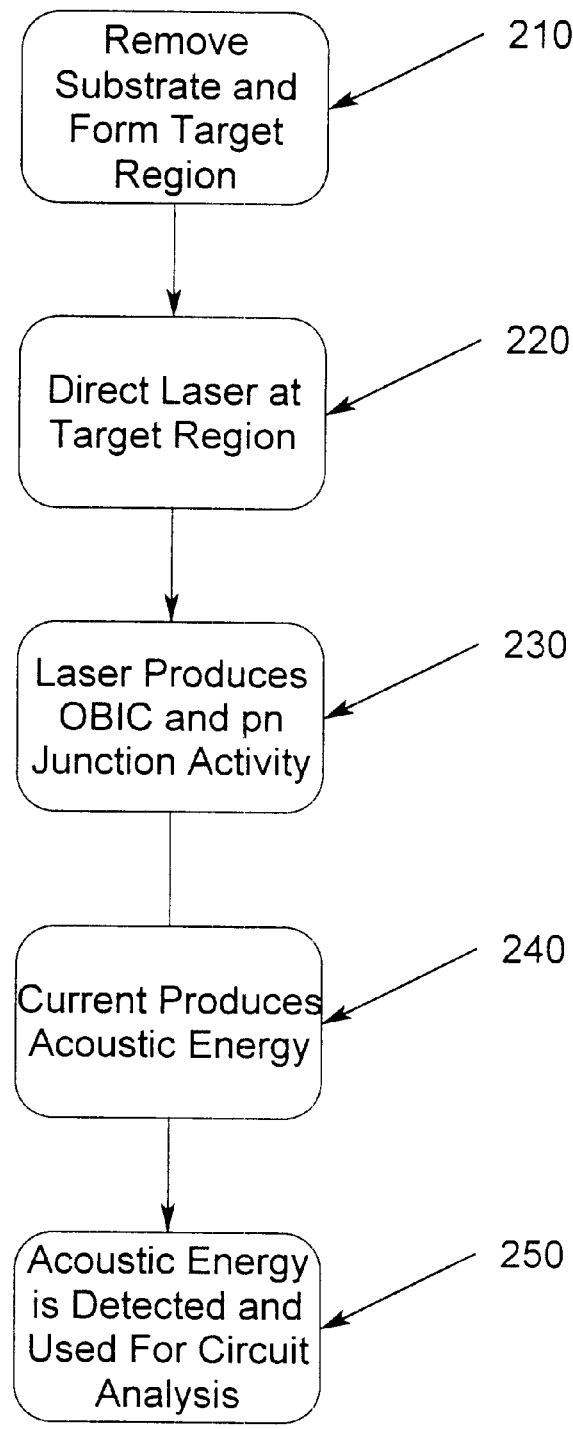
FIG. 2 is a flow diagram for a method of testing an integrated circuit device, according to another example embodiment of the present invention.

FIG. 2 is a flow diagram showing a method for analyzing a semiconductor device, according to another example embodiment of the present invention. Substrate is removed from a target region at block 210. A laser is directed at the target region at block 220 and produces OBIC and pn junction activity at block 230. The OBIC and pn junction activity produces acoustic energy in the device at block 240. The acoustic energy is detected at block 250 and used for circuit analysis.

In another example embodiment, a non-defective integrated circuit is thinned and an exposed region is formed. A laser is directed at the exposed region and OBIC is created, which in turn generates acoustic energy propagation in the device. At least one parameter corresponding to the acoustic propagation is determined and recorded as a standard parameter. The parameter may, for example, include amplitude, frequency, or phase information, and may include a spectrum. Using the recorded standard parameter or parameters of the non-defective die for comparison, an integrated circuit device is analyzed. The integrated circuit device is thinned and an exposed region is formed. A laser is directed at the exposed region of the device under test, and acoustic energy propagation is generated in the device. The propagation is detected, and a parameter corresponding to the propagation is determined. The parameter is then compared to the standard parameter to determine the existence of defects. For example, the standard parameter can be used in pass-fail testing, wherein the parameter from a device under test must about match the standard parameter if it is to pass.

In another example embodiment of the present invention, the integrated circuit device is thinned and an exposed region is formed at a predetermined thickness that corresponds to the substrate thickness used in establishing the parameter from a non-defective integrated circuit, as described herein. By thinning the substrate to the predetermined thickness, the laser incident upon the exposed region of the device under test is applied in a similar manner to the application of the laser to the non-defective device when the standard parameter was determined. In doing so, the resulting OBIC in the device under test is more closely related to the OBIC generated during the recordation of the standard parameter.

In the above example embodiments, directing a laser at an integrated circuit device may include pulsing the laser. Pulsing the laser can be accomplished by turning the laser on and off, or by otherwise varying the laser's intensity. By pulsing the laser, the amount of energy transferred to or induced in the device can be controlled. For example, as compared to using and applying a laser having a constant intensity over an uninterrupted period of time, pulsing the laser reduces the amount of energy transferred by the laser to the device. This method is particularly advantageous for exciting circuitry within the device and holding that circuitry at a particular energy level or level of activation, which is useful for testing the device. For instance, holding the circuitry at a particular power level can involve holding a pn junction just below the threshold required to turn the junction on, commonly referred to as the operating voltage. When it is desired to push the pn junction over the threshold an into operation, only a small amount of additional excitation is needed. In addition, pulsing the laser reduces the risk of overheating the device and melting metal in the device.

While the present invention has been described with reference to several particular example embodiments, those skilled in the art will recognize that many changes may be made thereto without departing from the spirit and scope of the present invention, which is set forth in the following claims.

What is claimed is:

1. A method for testing an integrated circuit, the method comprising:

detecting acoustic energy propagation in the integrated circuit; and detecting circuit defects as a function of the detected acoustic energy propagating in and current flowing in the integrated circuit.

2. A method for testing an integrated circuit, wherein the circuit has circuitry in a circuit side opposite a back side, the method comprising:

removing substrate from the back side and exposing a target region;

directing a laser at the target region, generating optical beam induced current (OBIC), and causing pn junction activity;

detecting acoustic energy propagation in the integrated circuit via at least one acoustic energy detector;

correlating the detected acoustic energy to a parameter; and detecting at least one defect in the circuit as a function of the correlated parameter.

3. A method for testing an integrated circuit, according to claim 2, wherein directing a laser at the target region in the back side of the integrated circuit includes using a laser having a wavelength of about 1064 nanometers.

4. A method for testing an integrated circuit, according to claim 2, wherein directing a laser at the target region in the back side of the integrated circuit includes pulsing the laser.

5. A method for testing an integrated circuit, according to claim 4, further comprising maintaining pn junctions near their operating voltage.

6. A method for testing an integrated circuit, according to claim 2, wherein the laser is synchronized with said at least one detector, and wherein detecting at least one defect includes detecting a phase shift of the correlated detected acoustic energy.

7. A method for testing an integrated circuit, according to claim 2, wherein correlating the detected acoustic energy to a parameter includes using a computer arrangement.

8. A method for testing an integrated circuit, according to claim 2, wherein detecting at least one defect in the circuit as a function of the correlated parameter includes detecting at least one of: an open circuit and a short circuit.

9. A method for testing an integrated circuit, according to claim 2, wherein detecting at least one defect in the circuit as a function of the correlated parameter includes comparing the correlated parameter to a standard parameter for a non-defective integrated circuit.

10. A method for testing an integrated circuit, according to claim 9, wherein detecting an acoustic energy propagation in the integrated circuit having a higher frequency and amplitude than the standard parameter indicates a short circuit.

11. A method for testing an integrated circuit, according to claim 9, wherein detecting an acoustic energy propagation in the integrated circuit having a lower frequency and amplitude than the standard parameter indicates an open circuit.

12. A method for testing an integrated circuit, according to claim 9, wherein removing substrate from the back side and exposing a target region includes removing an amount of substrate that corresponds to an amount of substrate removed from the non-defective integrated circuit when the standard parameter was ascertained.

13. A method for testing an integrated circuit, according to claim 2, wherein the integrated circuit is not powered.

14. A system for testing an integrated circuit having circuitry in a circuit side opposite a back side, the system comprising:

means for removing substrate from the back side;

a laser adapted to generate current in the integrated circuit;

means for detecting acoustic energy propagation in the integrated circuit;

means for correlating detected acoustic energy propagation to a parameter; and means for detecting at least one defect in the circuit using the correlated parameter.

15. A system for testing an integrated circuit having circuitry in a circuit side opposite a back side the system comprising:

a substrate removal device;

a laser configured and arranged to excite circuitry in the integrated circuit;

at least one acoustic energy detector adapted to detect acoustic energy in said integrated circuit; and a computer configured and arranged to correlate detected acoustic energy to a parameter that is used to detect at least one defect in the integrated circuit.

16. A system for testing an integrated circuit, according to claim 15, wherein the laser, said at least one acoustic energy detector, and the computer are communicatively coupled.

17. A system for testing an integrated circuit, according to claim 16, wherein the computer is configured and arranged to control the laser.

18. A system for testing an integrated circuit, according to claim 15, wherein the computer is further configured and arranged to detect at least one defect in the integrated circuit using the correlated detected acoustic energy.

19. A system for testing an integrated circuit, according to claim 18, wherein the computer is configured and arranged to detect at least one of: a short circuit and an open circuit.

* * * * *

UNITED STATES PATENT AND TRADEMARK OFFICE
CERTIFICATE OF CORRECTION

PATENT NO.      : 6,421,811 B1
DATED           : July 16, 2002
INVENTOR(S)     : Gorunganthu et al.

It is certified that error appears in the above-identified patent and that said Letters Patent is hereby corrected as shown below:

<u>Column 1,</u>
Line 10, after "Ser. No. 09/387,182" please insert -- , now U.S. Pat, No. 6,253,621, issued July 31, 2001 --.

<u>Column 2,</u>
Line 16, after "side" please insert -- . --.

Signed and Sealed this

Third Day of December, 2002

JAMES E. ROGAN
*Director of the United States Patent and Trademark Office*